(12) United States Patent
Song et al.

(10) Patent No.: US 11,134,976 B2
(45) Date of Patent: Oct. 5, 2021

(54) DEVICE HAVING A MULTI-CHANNEL TRANSMISSION MEMBER

(71) Applicant: Tao Song, Erie, PA (US)

(72) Inventors: Tao Song, Erie, PA (US); Shu Du, Erie, PA (US)

( * ) Notice: Subject to any disclaimer, the term of this patent is extended or adjusted under 35 U.S.C. 154(b) by 0 days.

(21) Appl. No.: 16/242,832

(22) Filed: Jan. 8, 2019

(65) Prior Publication Data

US 2019/0209198 A1 Jul. 11, 2019

Related U.S. Application Data

(60) Provisional application No. 62/614,740, filed on Jan. 8, 2018.

(51) Int. Cl.
| | |
|---|---|
| *A61B 17/32* | (2006.01) |
| *A61B 17/22* | (2006.01) |
| *A61M 25/00* | (2006.01) |
| *A61B 1/313* | (2006.01) |
| *A61B 1/00* | (2006.01) |
| *A61B 90/30* | (2016.01) |

(52) U.S. Cl.
CPC ......... *A61B 17/320068* (2013.01); *A61B 17/22012* (2013.01); *A61B 17/32002* (2013.01); *A61B 1/00154* (2013.01); *A61B 1/3132* (2013.01); *A61B 17/320016* (2013.01); *A61B 2017/22015* (2013.01); *A61B 2017/32007* (2017.08); *A61B 2017/320069* (2017.08); *A61B 2017/320072* (2013.01); *A61B 2017/320073* (2017.08); *A61B 2090/306* (2016.02); *A61B 2217/005* (2013.01); *A61B 2217/007* (2013.01); *A61M 2025/004* (2013.01)

(58) Field of Classification Search
CPC ...... A61B 17/320068; A61B 17/22012; A61B 17/32002; A61B 1/00154; A61B 2017/22015; A61B 2090/306; A61B 17/320016; A61B 2217/007; A61B 2017/320072; A61B 2017/320069; A61B 2017/320073; A61B 1/3132; A61B 2217/005; A61B 2017/32007; A61B 17/2202; A61B 18/24; A61B 2017/00106; A61M 2025/004; Y10T 29/49826; Y10T 29/49005; B29C 63/42
See application file for complete search history.

(56) References Cited

U.S. PATENT DOCUMENTS

| | | | | |
|---|---|---|---|---|
| 4,832,683 | A * | 5/1989 | Idemoto | ......... A61B 17/320068 604/22 |
| 4,867,141 | A * | 9/1989 | Nakada | ............ A61B 17/22012 601/4 |
| 5,163,421 | A * | 11/1992 | Bernstein | ............... A61B 8/481 606/128 |
| 5,320,617 | A | 6/1994 | Leach | |

(Continued)

*Primary Examiner* — Katherine M Shi
(74) *Attorney, Agent, or Firm* — The Webb Law Firm

(57) ABSTRACT

A compound transmission member including: a first tube sub-member and a second tube sub-member, each including: a first end having a first opening and a second end having a second opening, wherein the first opening is in fluid communication with the second opening, and wherein at least the first tube sub-member is configured to transmit ultrasonic energy; and a fitting configured to receive the first ends of the tube sub-members.

20 Claims, 11 Drawing Sheets

(56) References Cited

U.S. PATENT DOCUMENTS

| | | | |
|---|---|---|---|
| 6,482,218 B1 * | 11/2002 | Tran | A61B 17/22012 |
| | | | 606/169 |
| 9,173,667 B2 | 11/2015 | Du et al. | |
| 9,339,284 B2 | 5/2016 | Du et al. | |
| 9,763,684 B2 | 9/2017 | Du et al. | |
| 2004/0068189 A1 | 4/2004 | Wilson et al. | |
| 2008/0009848 A1 * | 1/2008 | Paraschiv | A61B 17/320068 |
| | | | 606/34 |
| 2009/0216125 A1 | 8/2009 | Lenker | |
| 2010/0317973 A1 | 12/2010 | Nita | |
| 2011/0082396 A1 | 4/2011 | Wallace | |
| 2011/0196398 A1 * | 8/2011 | Robertson | A61B 17/32002 |
| | | | 606/169 |
| 2015/0005771 A1 * | 1/2015 | Voic | A61B 17/320068 |
| | | | 606/79 |
| 2016/0022306 A1 | 1/2016 | Du et al. | |
| 2016/0235424 A1 | 8/2016 | Du et al. | |
| 2018/0235650 A1 * | 8/2018 | Beaupre | A61B 17/320092 |
| 2020/0268397 A1 * | 8/2020 | Brouillette | A61B 17/22012 |

* cited by examiner

DEVICE HAVING A MULTI-CHANNEL TRANSMISSION MEMBER

CROSS-REFERENCE TO RELATED APPLICATION

This application claims priority to U.S. Provisional Patent Application No. 62/614,740, filed on Jan. 8, 2018, the disclosure of which hereby is incorporated by reference in its entirety.

BACKGROUND OF THE DISCLOSURE

Field of the Disclosure

The present disclosure relates generally to apparatus, systems, and methods used in conjunction with an ultrasonic ablation device and, more specifically, systems and methods relating to a compound transmission member having one or more tube sub-members to transfer ultrasonic energy to body tissue from an ultrasonic energy source.

Description of Related Art

Examples of apparatus and methods for transferring ultrasonic energy to body tissue are discussed in U.S. Pat. No. 9,339,284 to Du et al.; U.S. Pat. No. 9,173,667 to Du et al.; U.S. Pat. No. 9,763,684 to Du et al.; United States Patent Application Publication No. 2016/0022306 to Du et al.; and United States Patent Application Publication No. 2016/0235424 to Du et al., which are incorporated by reference as if fully restated herein.

Known ultrasonic energy transmission systems are used in many different medical applications, such as, for example, medical imaging, to disrupt obstructions and/or ablate bodily tissue. In known ultrasonic energy transmission systems for tissue ablation, ultrasonic energy is transferred from an ultrasonic energy source through a transducer horn and then a single transmission member, such as a wire, to a distal head. Ultrasonic energy propagates through the transmission member as a periodic wave thereby causing the distal end or distal head to vibrate. Such vibrational energy can be used to ablate or otherwise disrupt body tissue, for example, a vascular obstruction, a kidney stone or the like. To effectively reach various sites for treatment of intravascular occlusions or regions within the urinary tract, such ultrasonic transmission members often have lengths of about 25 cm or longer.

Known ultrasonic transmission members are constructed to be flexible enough to be passed through various bodily lumens, but also with sufficient strength to transmit ultrasonic energy to the distal tip (e.g., to ablate vascular or urinary obstructions). A stronger, more durable transmission member allows for greater transmission of energy, but may not be flexible enough to be advanced through the vasculature to a desired treatment area. In known configurations having single transmission members, a thinner transmission member can be more flexible, but is less durable and more susceptible to breakage. Additionally, when a suction force is desired to remove fluid or ablated tissue from a body cavity, a thin single transmission member may not have sufficient flux to provide sufficient suction.

Ultrasonic ablation systems include a single transmission member. To balance strength and flexibility, the single transmission member can have legate openings along the length of the transmission member. Such transmission members must be coated with a sheath in order to apply a suction force.

Another option to increase flexibility is to have a tapered longitudinal axis of the transmission member such that the diameter of the distal end portion decreases to allow greater flexibility. The tapered transmission member can include a distal tip or "head" that is welded to the reduced diameter section, and which is positioned adjacent the tissue to be treated. Such transmission members can be prone to breakage at or near the distal end of the transmission member where the cross-sectional area of the transmission member becomes smaller and/or at the discontinuous region where the two pieces are joined. Similarly stated, such breakage is generally caused by stress concentration due to transverse vibrations and fatigue. Thus, one difficulty related to transmission of ultrasonic energy through a relatively long transmission member of known design is premature wear and breakage of the transmission member.

Furthermore, the coupling of the distal head to the distal end of the transmission member results in a discontinuity between the transmission member and the distal head due to the weld material, adhesive material, or the like. Such discontinuities can produce reflections of the ultrasonic wave and result in losses of ultrasonic energy. To overcome the energy losses, the level of ultrasonic energy applied and transferred through the transmission member can be increased. The increase in the ultrasonic energy transferred through the transmission member can increase stress on the transmission member and, consequently, can result in premature fatigue and breakage.

Thus, a need exists for an improved apparatus and methods for transferring ultrasonic energy from an ultrasonic energy source to a target body tissue.

SUMMARY OF THE INVENTION

A compound transmission member includes a first tube sub-member and a second tube sub-member. The first tube sub-member includes a first end having a first opening and a second end having a second opening. The second tube sub-member includes a first end having a first opening and a second end having a second opening. The first opening of first sub-member and second sub-member is in fluid communication with the second opening of the first sub-member and the second sub-member. At least the first tube sub-member is configured to transmit ultrasonic energy. A fitting is configured to receive the first end of the first tub sub-member and second tube-sub-member at the first end of the first tube sub-members and the first end of the second tube sub-member.

A method for ablating a target tissue includes the steps of producing ultrasonic energy at a source. A compound transmission member is operatively connected to the source. The compound transmission member includes a first tube sub-member and a second tube sub-member. The first tube sub-member and the second tube sub-member each include a first end having a first opening and a second end having a second opening. The first opening is in fluid communication with the second opening. At least the first tube sub-member is configured to transmit ultrasonic energy. A fitting is configured to receive the first end of the first tube sub-member and the first end of the second tube sub-member. The first tube sub-member and second tube sub-member are sufficiently flexible to move along a tortuous path in a body cavity. The second end of the first tube sub-member and second end of the second tube member is inserted into the body cavity. The first tube sub-member and second tube sub-member move along the tortuous path. The first end of the first tube sub-member is proximal to the target tissue. The ultrasonic energy is applied to the target tissue. The ultrasonic energy is applied to the target tissue through the first tube sub-member.

Various aspects of the system and method for a compound transmission member having one or more tube sub-members are disclosed in one or more of the following numbered clauses:

Clause 1. A compound transmission member comprises: a first tube sub-member and a second tube sub-member, each comprising: a first end having a first opening and a second end having a second opening, wherein the first opening is in fluid communication with the second opening, and wherein at least the first tube sub-member is configured to transmit ultrasonic energy; and a fitting configured to receive the first ends of the tube sub-members.

Clause 2: The compound transmission member according to clause 1, wherein the first tube sub-member and the second tube sub-member are attached to the fitting.

Clause 3: The compound transmission member according to clause 2, wherein the first and second tube sub-members are attached to the fitting by at least one of brazing, welding, and adhesive.

Clause 4: The compound transmission member according to any of clauses 1 to 3, further comprising an outer sheathing enclosing at least a portion of the compound transmission member.

Clause 5: The compound transmission member according to any of clauses 1 to 4, wherein the first tube sub-member is monolithically constructed.

Clause 6: The compound transmission member according to any of clauses 1 to 5, wherein the compound transmission member is sufficiently flexible to move along a tortuous path in a body cavity.

Clause 7: The compound transmission member according to any of clauses 1 to 6, further comprising a cutting member extending from the second end portion of the first tube sub-member and configured to ablate a target tissue.

Clause 8: The compound transmission member according to clause 7, wherein the cutting member comprises at least one sharpened cutting edge.

Clause 9: The compound transmission member according to any of clauses 7 to 8, wherein the cutting member is welded, brazed, or glued to the first tube sub-member.

Clause 10: The compound transmission member according to any of clauses 7 to 8, wherein the cutting member is integrally formed on the second end of the first tube sub-member.

Clause 11: The compound transmission member according to any of clauses 7 to 10, wherein the cutting member comprises a flat hook member.

Clause 12: The compound transmission member according to any of clauses 7 to 11, wherein the cutting member comprises a bent tube hook member, the bent tube hook member comprising: an extension portion extending from the second end portion of the first tube sub-member in a direction away from a longitudinal axis of the first tube sub-member; and a first cutout portion in the extension portion defining a cutting edge.

Clause 13: The compound transmission member according to any of clauses 7 to 12 wherein the cutting member comprises a straight tube hook member, the straight tube hook member comprises: an extension portion extending from the second end portion of the first tube sub-member in a direction along a longitudinal axis of the first tube sub-member; and a first cutout portion in the extension portion defining a cutting edge.

Clause 14: The compound transmission member according to clause 13, wherein the second tube sub-member comprises a bent configuration extending from the second end portion of the second sub-member, wherein the bent configuration defines a lumen in fluid communication with the first opening in the first end of the second tube sub-member; and an end opening in fluid communication with the lumen of the bent configuration, wherein the end opening is oriented along the longitudinal axis of the first tube sub-member.

Clause 15: The compound transmission member according to any of clauses 1 to 14, wherein tube sub-members define an outer diameter of at least 1 millimeter, and no more than 2 millimeters.

Clause 16: The compound transmission member according to any of clauses 1 to 6, further comprises: a third through seventh tube sub-member configured to transmit ultrasonic energy, each comprising a first end having a first opening and a second end having a second opening, wherein the first opening is in fluid communication with the second opening; wherein the second tube sub-member defines an elongated device passage between the first opening and the second opening configured to allow an optical device to pass from the first end to the second end; wherein the second end of the first and third-through seventh tube sub-members are configured to focus ultrasonic energy at a point that is distal from the second end portions of the tube sub-member; wherein the fitting is configured to receive the first ends of the tube sub-members and comprises an opening and a first lumen in fluid communication with the opening and the elongated device passage; and wherein the opening and the first lumen are configured to allow a user to insert an optical device into the device passage.

Clause 17: The compound transmission member according to any of clauses 1 to 15, comprising three tube sub-members, each tube sub-member defining an outer diameter of at least 0.9 millimeters and no more than 1.8 millimeters.

Clause 18: The compound transmission member according to any of clauses 1 to 15, comprising four tube sub-members, each tube sub-member defining an outer diameter of at least 0.8 millimeters and no more than 1.6 millimeters.

Clause 19: The compound transmission member according to any of clauses 1 to 15, comprising five tube sub-members, each tube sub-member defining an outer diameter of at least 1.1 millimeters and no more than 1.4 millimeters.

Clause 20: The compound transmission member according to any of clauses 1 to 15, comprising six tube sub-members, each tube sub-member defining an outer diameter of at least 0.9 millimeters and no more than 1.3 millimeters.

Clause 21: The compound transmission member according to any of clauses 1 to 16, comprising seven tube sub-members, each tube sub-member defining an outer diameter of at least 0.8 millimeters and no more than 1.2 millimeters.

Clause 22: The compound transmission member according to any of clauses 1 to 16, comprising more than seven sub-members, wherein each sub-member is a wire sub-member defining an outer diameter of at least 0.1 millimeters, and no more than 1.0 millimeters.

Clause 23: The compound transmission member according to any of clauses 1 to 22, wherein the fitting comprises a first end and a second end, wherein the first end of the fitting is configured to receive the first ends of the tube sub-members; and wherein the second end is configured to operatively engage a transducer horn.

Clause 24: The compound transmission member according to any of clauses 1 to 21 and 23, wherein at least the first tube sub-member is configured to apply a suction force during ablation of a target tissue.

Clause 25: The compound transmission member according to any of clauses 1 to 15, 17 to 20, and 23-24, wherein the second tube sub-member defines an elongated device passage between the first opening and the second opening configured to allow an optical device to pass from the first end to the second end.

Clause 26: The compound transmission member according to clause 25, wherein the fitting further comprises an opening and a first lumen in fluid communication with the opening and the elongated device passage, and wherein the opening and the first lumen are configured to allow a user to insert an optical device into the device passage.

Clause 27: A method for ablating a target tissue comprising: producing ultrasonic energy at a source; supplying ultrasonic energy to a compound transmission member operatively connected to the source, wherein the compound transmission member comprises a first tube sub-member and a second tube sub-member each comprising: a first end having a first opening and a second end having a second opening, wherein the first opening is in fluid communication with the second opening, wherein at least the first tube sub-member is configured to transmit ultrasonic energy, a fitting configured to receive the first ends of the tube sub-members, and wherein the first and second tube sub-members are sufficiently flexible to move along a tortuous path in a body cavity; inserting the second ends of the first and second tube members into the body cavity; moving the first and second tube sub-members along the tortuous path; positioning the first ends of the tube members proximal to the target tissue; and applying ultrasonic energy to the target tissue.

Clause 28: The method according to clause 27, further comprising the step of applying a suction force via at least the first tube member.

Clause 29: The method according to any of clauses 27 and 28, wherein the second tube sub-member further comprises an elongated device passage between the first opening and the second opening configured to allow an optical device to pass from the first end to the second end; wherein the fitting further comprises an opening and a first lumen in fluid communication with the opening and the elongated device passage, wherein the opening and the first lumen are configured to allow a user to insert an optical device into the device passage; and further comprising the step of inserting the optical device into the body cavity through the opening, lumen, and elongated device passage of the second tube sub-member.

These and other features and characteristics of systems and methods relating to a compound transmission member having one or more sub-members, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only.

DETAILED DESCRIPTION

Figure 1:
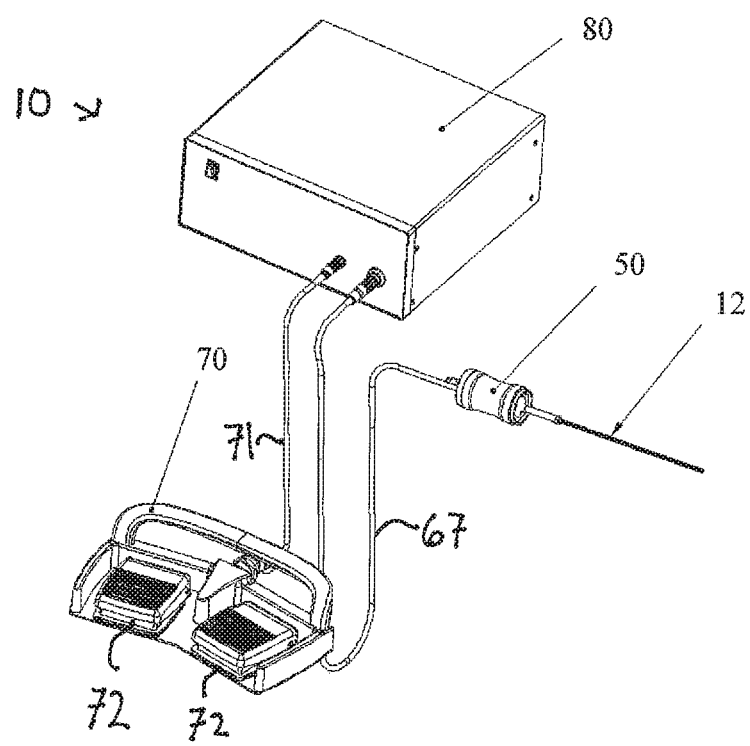
FIG. 1 is perspective view of a system for delivering ultrasonic energy to body tissue consistent with the present disclosure.

As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "includes" is synonymous with "comprises".

When used in relation to a compound transmission member, the term "proximal" refers to a portion of transmission member that is oriented for connecting to a transducer horn. The term "distal" refers to a portion of transmission member farthest away from a transducer horn when the transmission member is oriented for connecting to the transducer horn. The term "radial" refers to a direction in a cross-sectional plane normal to a longitudinal axis of transmission member. The term "circumferential" refers to a direction around an inner or outer surface of a sidewall of a transmission member. The term "axial" refers to a direction along a longitudinal axis of a transmission member extending between the proximal and distal ends.

It is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the examples disclosed herein are not to be considered as limiting.

Referring to the drawings in which like reference characters refer to like parts throughout the several views thereof, the present disclosure is generally directed to apparatus, systems and methods used in conjunction with an ultrasonic ablation device and, more specifically, apparatus, systems and methods relating to a compound transmission member having one or more tube sub-members.

For example, FIG. 1 is an example of an ultrasonic energy ablation system 10, according to the present disclosure. The ultrasonic energy ablation system 10 (also referred to herein as "ultrasonic system" or simply "system") includes an ultrasonic generator 80, a foot switch 70, an ultrasonic transducer assembly 50, and a transmission member 12. The ultrasonic generator 80 (or "generator") can be any suitable generator configured to generate, control, amplify, and/or transfer an electric signal (e.g., a voltage) to the transducer assembly 50.

The ultrasonic generator 80 may include at least a processor, memory, and the circuitry (not shown in FIG. 1) to produce an electronic signal (such as a current and a voltage) having the desired characteristics that can be received by the ultrasonic transducer assembly 50 and converted into ultrasonic energy. In some examples, the ultrasonic generator 80 can be electrically coupled to (e.g., "plugged into") an electric receptacle such that the ultrasonic generator 80 receives a flow of electric current. For example, in some embodiments, the ultrasonic generator 80 can be plugged into a wall outlet that delivers alternating current (AC) electrical power at a given voltage (e.g., 120V, 230V, or other suitable voltage) and a given frequency (e.g., 60 Hz, 50 Hz, or other suitable frequency).

Although not shown in FIG. 1, the ultrasonic generator 80 may include electronic circuitry, hardware, firmware and or instructions to cause the ultrasonic generator 80 to act as a frequency inverter and/or voltage booster. In this manner, the ultrasonic generator 80 can produce and/or output a voltage to the transducer assembly 50 having the desired characteristics to produce the desired ultrasonic energy output. In some non-limiting examples, the ultrasonic generator 80 can receive AC electrical power at a frequency of approximately 60 Hz and a voltage of approximately 120V and convert the voltage to a frequency up to approximately 20,000 Hz to 35,000 Hz with a voltage of approximately 500-1500 VAC (RMS). In some examples, frequencies may reach 50,000 Hz. Thus, the ultrasonic generator 80 can supply the transducer assembly 50 with a flow of AC electrical power having an ultrasonic frequency.

As shown in FIG. 1, the system 10 includes the foot switch 70 that is in electric communication with the ultrasonic generator 80 via a foot switch cable 71. The foot switch 70 includes a set of pedals 72 (e.g., two pedals as shown) that are operative in controlling the delivery of the ultrasonic electrical energy supplied to the ultrasonic transducer assembly 50. In some examples, a user (such as a physician, nurse, technician, etc.) can engage and/or depress one or more of the pedals 72 to control the current supplied to the ultrasonic transducer assembly 50 such that, in turn, the transmission member 12 delivers the desired ultrasonic energy to the bodily tissue, as further described in detail herein.

The transducer assembly 50 is in electric communication with the ultrasonic generator 80 via a transducer cable 67. The transducer assembly 50 can receive an electrical signal (i.e., voltage and current) from the ultrasonic generator 80 via the transducer cable 67. The transducer assembly 50 is configured to produce the desired ultrasonic energy via a set of piezoelectric members 1162 (i.e., piezoelectric rings) and a transducer horn 1163 (see e.g., FIG. 2), and transfer the ultrasonic energy to the transmission member 12. The transducer assembly 50 can be any suitable assembly of the types shown and described herein. In other embodiments consistent with the present disclosure, the transducer assembly 50 may produce desired ultrasonic energy via one or more electromagnets.

Figure 2:
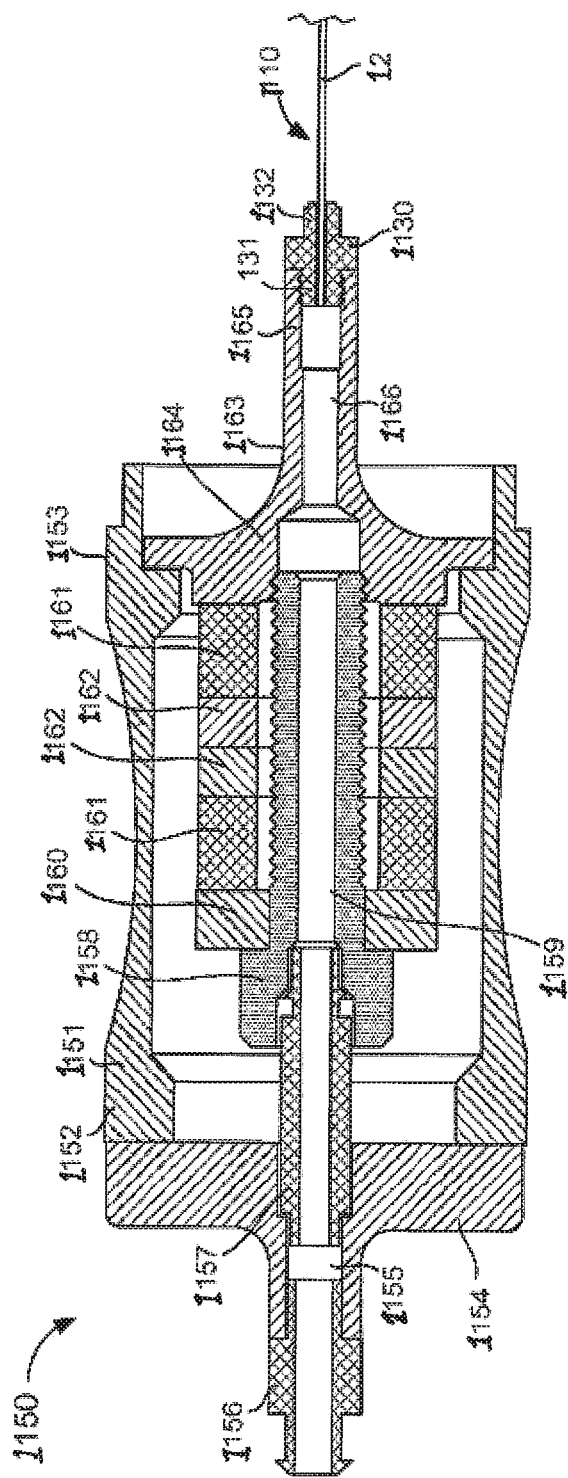
FIG. 2 is a cross-sectional view of an ultrasonic transducer included in the system of FIG. 1.

With reference to the non-limiting example shown in FIG. 2, a transducer assembly 1150 includes a housing 1151 having a proximal end portion 1152 and a distal end portion 1153. The housing 1151 is configured to house or otherwise enclose at least a portion of a flow tube 1157, a bolt 1158, a back plate 1160, a set of insulators 1161, a set of piezoelectric rings 1162, and a transducer horn 1163.

The proximal end portion 1152 of the housing 1151 is coupled to a proximal cover 1154 (e.g., via an adhesive, a press or friction fit, a threaded coupling, a mechanical fastener, or the like). The proximal cover 1154 defines an opening 1155 such that the proximal cover 1154 can receive a portion of a connector 1156 (in examples, a luer connector) on a proximal side thereof (e.g., substantially outside the housing 1151) and a portion of the flow tube 1157 on a distal side thereof (e.g., substantially inside the housing 1151). Expanding further, the proximal cover 1154 can receive the connector 1156 and the flow tube 1157 such that the proximal cover 1154 forms a substantially fluid tight seal with the connector 1156 and the flow tube 1157. A vacuum can be applied via the connector 1156 to irrigate and/or aspirate the region of the body within which the transmission member 12 is disposed. Similarly stated, this arrangement results in the connector 1156 being placed in fluid communication with a lumen defined by a transmission member 12.

The distal end portion 1153 of the housing 1151 is configured to receive the transducer horn 1163 such that the transducer horn 1163 is coupled to an inner surface of the housing 1151. The transducer horn 1163 can be disposed at least partially within the housing 1151 such that the transducer horn 1163 can be moved relative to the housing 1151 (for example, when amplifying the ultrasonic energy), but not moved out of the housing 1151 during normal use. The transducer horn 1163 includes a proximal end portion 1164 and a distal end portion 1165 and defines a lumen 1166 therethrough. The lumen 1166 is configured to receive a portion of the bolt 1158 at the proximal end portion 1164 of the transducer horn 1163 and a portion of the transmission member 12 at the distal end portion 1165 of the transducer horn 1163, both of which are described in further detail herein.

The bolt 1158 further may define a lumen 1159 such that a proximal end portion of the bolt 1158 can receive a distal end portion of the flow tube 1157. The lumen 1159 defined by the bolt 1158 and the flow tube 1157 collectively place the lumen 1166 defined by the transducer horn 1163 in fluid communication with the connector 1156. Thus, the lumen 1166 of the transducer horn 1163 can be placed in fluid communication with a volume substantially outside of the proximal end of the housing 1151.

With continued reference to FIG. 2, the transmission member 12 may engage the transducer horn 1163 via a fitting 1130. The fitting 1130 includes a proximal end portion 1131 and a distal end portion 1132 and defines a lumen 1133 that extends therethrough. The proximal end portion 1131 of the fitting 1130 is disposed within the lumen 1166 at the distal end portion 1165 of the transducer horn 1163 and may form a threaded fit with the inner surface of the transducer horn 1163 that defines the lumen 1166. The distal end portion 1131 of fitting 1130 may be configured to receive a portion of the transmission member 12 to fixedly couple the transmission member 12 to fitting 1130. In this manner, the transmission member 12 can be removably coupled to the transducer assembly 1150 via the fitting. As show in FIG. 14, examples of the fitting 830 may include an aperture fluidly connected to a device passage 850 configured to conduct an optical device (not shown) to a target tissue in a body cavity. Examples of the aperture 852 and device passage 850 may be fluidly isolated from the flow tube 1157. Examples of the aperture 852 may be located on the fitting 1130 or the housing 1151 of the transducer assembly 1150.

With reference to FIGS. 1 and 2, a user, such as a surgeon, a nurse, a technician, physician, etc., can operate the ultrasonic system 10 to deliver ultrasonic energy to a target bodily tissue within a patient. The user can, for example, engage the pedals 72 of the foot switch 70 such that the ultrasonic generator 80 generates an alternating current (AC) and voltage with a desired ultrasonic frequency (in an example, 20,000 Hz). In this manner, the ultrasonic generator 80 can supply AC electric power to the piezoelectric rings 1162, or other source of ultrasonic energy, such as one or more electromagnets. The AC electric power can urge the piezoelectric rings 1162 to oscillate (e.g., expand, contract, or otherwise deform) at the desired frequency, which, in turn, causes the transducer horn 1163 to move relative to the housing 1151. Thus, with the transmission member 12 coupled to the transducer horn 1163, the movement of the transducer horn 1163 vibrates and/or moves the transmission member 12. In this manner, a distal end portion of the transmission member 12 can be disposed with a portion of the patient adjacent to a target tissue such that the transmission member 12 transfers at least a portion of the ultrasonic energy to the target tissue (not shown in FIGS. 1 and 2). For example, in some embodiments, a distal end of the transmission member 12 can impact a target tissue such as, for example, to break apart an occlusion. In some examples, the movement of the distal end portion of the transmission member 12 is such that cavitations occur within the portion of the patient. In this manner, the cavitations can further break apart a target tissue. In some embodiments, the ultrasonic system 10 can optionally be used to aspirate and/or to supply irrigation to a target tissue site.

Figure 3:
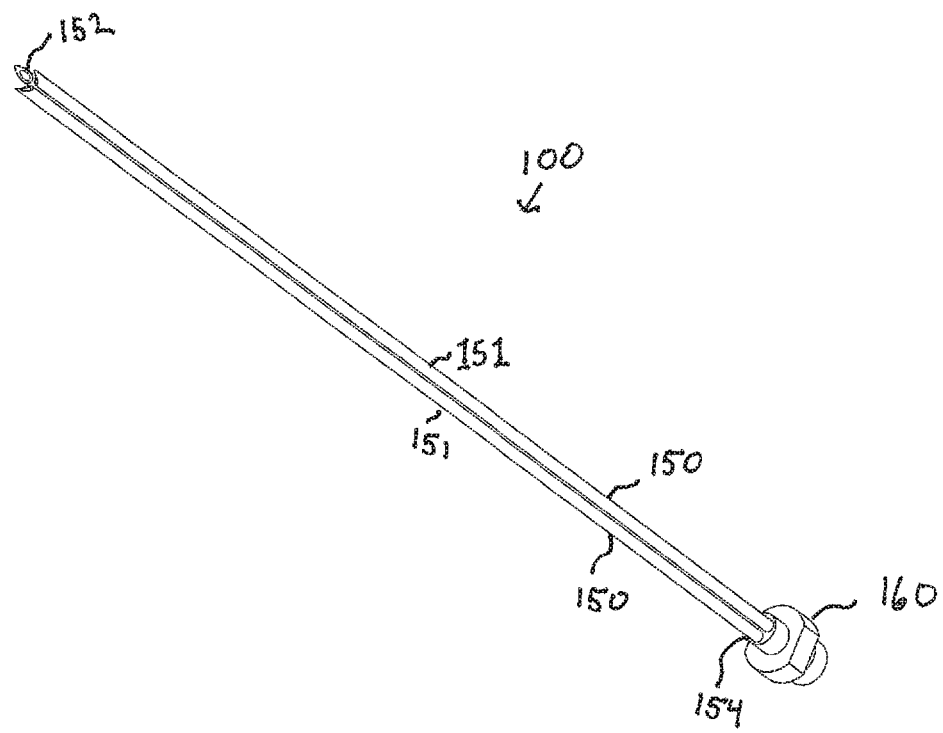
FIG. 3 is a perspective view of an example of a compound transmission member consistent with the present disclosure.

The transmission member 12 may be a compound transmission member having a proximal end portion and a distal end portion, and comprising a plurality of sub-member. FIG. 3. shows an example of a compound transmission member 100 consistent with the present disclosure. The compound transmission member 100 according to FIG. 3 includes three tube sub-members 150. Each tube sub-member 150 includes an elongate tube having a sidewall 151, a first, proximal end 154 and a second, distal end 152, and is configured to be inserted into a body cavity. A lumen 158 is defined by the each elongate tube, and establishes fluid communication between an opening in the first proximal end 154 and a distal opening 156 disposed in the second distal end 152 of the tube sub-member 150. The proximal end 154 of each tube sub-member 150 may be fixedly coupled to a fitting 160, which may be removably coupled with a transducer horn 1163, as in FIG. 2. Examples of the compound transmission member 100 may be any suitable shape, size, stiffness, or configuration and is described in further detail herein.

With further reference to FIG. 3, each tube sub-member 150 affixed to the fitting 160 by brazing, welding, and adhesive, or another manner known in the art. Similarly, some or all of the tube sub-members 150 may be attached to another tube sub-member 150 by brazing, welding, and adhesive, or another manner known in the art, along all or portions of their respective sidewalls 151. In other examples, it may be preferable for the tube sub-members 150 not to be attached to other tube sub-members 150 of the transmission member 100 along the sidewalls 151 thereof. In some examples, the tube sub-members 150 may be enclosed by a flexible sheath, such as a thin plastic sheath, not shown.

Each tube sub-member 150 of the compound transmission member 100 may be comprised of a material, such as metal, capable of transmitting ultrasonic energy from the proximal end 154 to the distal end 152 and configured to ablate a target tissue in a body cavity. The tube sub-members 150 further have sufficient flexibility to facilitate the passage of the transmission member 100 through a tortuous lumen or path within a patient. For example, in some examples, a compound transmission member 100 can have a suitable flexibility such that at least a portion of the transmission member can elastically (e.g., not permanently) deform within the tortuous anatomical structure.

As used herein, the term "flexibility" relates to the ease with which an object deflects, deforms, and/or displaces due to the application of an external force. This is generally the opposite of "stiffness," which relates to an object's resistance to deflection, deformation, and/or displacement produced by an applied force. A sidewall of a transmission member or tube sub-member with greater stiffness is more rigid, or resistant to deflection, deformation and/or displacement when exposed to a force than a wall of a tube having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different than the portion of the object to which the force is directly applied.

Stiffness and flexibility are dependent upon the material from which the object is formed, as well as certain physical characteristics of the object (e.g., cross-sectional shape, length, boundary conditions, etc.). For example, the stiffness of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force.

The stiffness of an object also can be increased or decreased by changing a physical characteristic of the object, such as the shape or cross-sectional area of the object. For example, an object having a length and a cross-sectional area may have a greater stiffness than an object having an identical length but a smaller cross-sectional area. The stiffness of an object can be decreased by, among other things, decreasing the cross-sectional area of an object.

The stiffness (or inversely, the flexibility) of an elongated object, such as a catheter or tube can be characterized by its flexural stiffness. The flexural stiffness of an object can be used to characterize the ease with which the object deflects under a given force (e.g., the ease with which the object deflects when the object is moved along a tortuous path within the body). The flexural stiffness of an object, such as a catheter, transmission member or the like, can be mathematically expressed as shown in Equation 1, below:

$$k = \frac{3EI}{L^3}$$

where k is the flexural stiffness of the object, E is the modulus of elasticity of the material from which the object is constructed, I is the area moment of inertia of the object, and L is the length of the object.

As used herein, the terms "cross-sectional area moment of inertia," or "area moment of inertia," relate to an object's resistance to deflection or displacement around an axis that lies in a cross-sectional plane. The area moment of inertia is dependent on the cross-sectional area and/or shape of the object, and can be mathematically expressed as a function of a cross-section of the object. The area moment of inertia of an object (e.g., such as the tubes disclosed herein) is described having units of length to the fourth power (e.g., in$^4$, mm$^4$, etc.). The formula used to define an area moment of inertia for an object having a substantially annular cross-section is expressed in Equation 2:

$$I = \frac{\pi(d_o^4 - d_i^4)}{64}$$

where $d_o$ is the outer diameter of the annulus, and $d_i$ is the inner diameter of the annulus. Thus, substituting the equation for area moment of inertia into the equation for flexural stiffness, it can be seen that, between two objects having the same composition, and the same length, and each having annular cross sections of the same thickness, the object with the smaller outer diameter will have more flexibility than the object with the larger outer diameter. Thus, a compound transmission member having multiple sub-members may be more flexible than a transmission member having a single tube of larger diameter.

With continued reference to FIG. 3, examples of the tube sub-members 150 may be formed from any suitable material such as, for example, Type 304 stainless steel, Type 316 stainless steel, nickel titanium alloy (nitinol), or any other super elastic metal or metal alloy. Each tube sub-member 150 may be formed of different materials or the same materials, as may various portions of the tube sub-members 150. Examples of tube sub-members may be monolithically formed of a substantially uniform material. While three tube sub-members 150 are shown in FIG. 3, it is to be understood that examples of compound transmission member 100 may have more or fewer tube sub-members 150.

Figure 4:
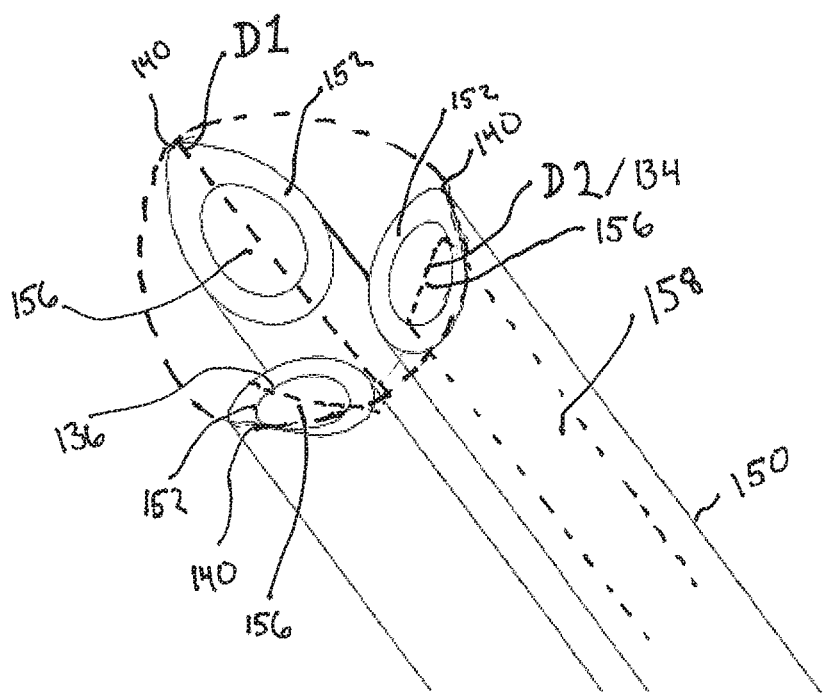
FIG. 4 is a perspective view of a distal end of the example of a compound transmission member of FIG. 3.

FIG. 4 depicts the distal portion of the compound transmission member 100 of FIG. 3. The distal end of the compound transmission member 100 is configured to apply ultrasonic energy transmitted from a transducer assembly 1150, as in FIG. 2, to a target tissue for ablation. Each tube sub-member 150 defines a lumen 158 that establishes fluid communication between the distal end 152, and openings disposed on the proximal ends 154 of the tube sub-members 150. Each lumen has a diameter that defines an internal diameter 134 of each tube sub-member 150. The outer surface of a sidewall 151 of the tube sub-member defines an external diameter 136 of that tube sub-member 150. In examples, each tube sub-member 150 may have substantially similar internal diameters 134 and/or external diameters 136. In other examples, the internal diameters 134 and/or external diameters 136 may be substantially different between tube sub-members 150. Examples of tube sub-members 150 may have substantially uniform internal diameters 134 and/or external diameters 136 along the length of their sidewalls 151. In other examples, a tube sub-member 150 may have internal diameters 134 and/or external diameters 136 that vary according to a gradient, or define specific infection points having a lower or higher area moment of inertia than other portions of the tube sub-member.

With continued reference to FIGS. 3 and 4, the compound transmission member 100 has an exterior diameter D1. As shown by Equations 1 and 2, each tube sub-member 150 has a lower area moment of inertia—and thus, greater flexibility—than a hypothetical monolithic transmission member made of the same material, and having the same exterior diameter D1 and internal diameter of compound transmission member 100. Thus, a compound transmission member 100 according to the present disclosure may have improved flexibility over prior examples of monolithic transmission members.

With further reference to FIGS. 3 and 4, the distal ends 152 of each tube sub-member 150 may be shaped with apply parts 140 configured to engage the target tissue to be ablated. Examples of apply parts 140 may be angled or protruding with respect to an annular cross-section of the tube sub-member 150. This may allow high-efficiency fragmentation of body tissue with ultrasonic energy transmitted by the transmission member by limiting to application of ultrasonic energy to a target tissue.

With continued reference to FIGS. 3 and 4, lumens 158 in fluid communication with distal openings 156 may allow the tube sub-members 150 to aspirate debris and/or irrigate a fluid flow during the applications of ultrasonic vibrations through the tube sub-members 150.

Figure 5:
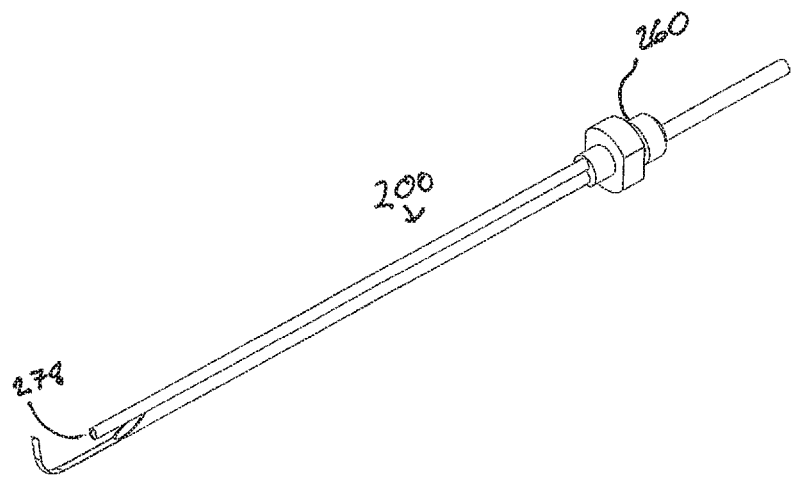
FIG. 5 is a perspective view of an example of a compound transmission member having a flat hook member consistent with the present disclosure.
Figure 6:
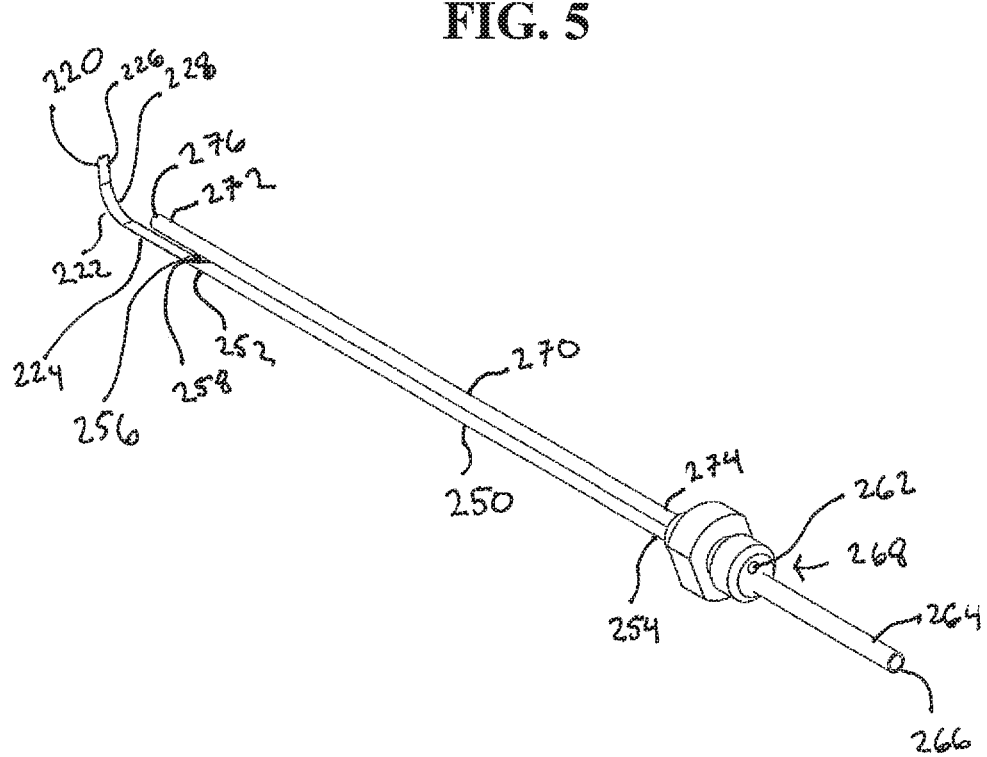
FIG. 6 is another view of the example of the compound transmission member of FIG. 5.

FIGS. 5 and 6 show another example of a transmission member 200 according to the present disclosure. The transmission member 200 of FIGS. 5 and 6 comprise a first tube sub-member 270, and a second tube sub-member 250, although it is to be understood that other examples consistent with this disclosure may include more tube sub-members. Each tube sub-member 270, 250, may be brazed, glued, welded, adhered, or otherwise affixed to a fitting 260. The fitting may be threaded or otherwise configured to fixedly engage a transducer assembly 1150, as in FIG. 2, and the fitting 260 and first and second tube sub-members 270, 250, may be configured to transmit and apply ultrasonic energy from a transducer assembly to a target body tissue, and a sufficiently flexible to navigate a tortious body cavity to reach a target body tissue.

With continued reference to FIGS. 5 and 6, first tube sub-member 270 comprises a distal end 272 and a proximal end 274. A distal opening 276 is disposed in the distal end 272 of first tube sub-member 270, and first tube sub-member 270 defines a lumen in fluid communication with the distal opening 276 and an opening at proximal end 274. Similarly, second tube sub-member 250 comprises a distal end 252 and a proximal end 254. A distal opening 256 is disposed on the distal end 252 of second tube sub-member 250, and tube sub-member 250 defines a lumen in fluid communication with the distal opening 256 and an opening in the proximal end 254. In examples, either or both of first and second tube sub-members 270, 250 may aspirate debris or irrigate a fluid flow during the applications of ultrasonic vibrations though the transmission member 200.

In examples, second tube sub-member 250 may not be brazed, welded, adhered, or otherwise fixedly attached to the fitting 260, but instead may be configured to be removable attached to an aperture (not shown) in fitting 260. Examples of tube sub-member 250 may be longitudinally inserted into the aperture in the fitting 260. In examples, the aperture in the fitting, may have internal threads that co-act with external threads on a portion of the second tube sub-member 250 to engage the second tube sub-member 250 in the fitting 260. Examples of second tube sub-member also may be longitudinally inserted into fitting 260 and held in place with a friction fit. Examples of second tube sub-member 250 still may be configured to transmit ultrasonic energy to a target body tissue.

With continued reference to FIGS. 5 and 6, a cutting member comprising a flat hook member 220 extends from the distal end 252 of second tube sub-member 250. A first portion 224 of the flat hook member 220 extends substantially distally from the distal end 252 of tube sub-member 250, and a second portion 226 of the flat hook member 220 may extend in a different direction from the first portion 224. In an example, the second portion 226 may extend in a substantially perpendicular direction from the first portion 224. The first portion 224 and second portion 226 of the flat hook member 220 are connected by a curved portion 228 that transitions between the orientations of the first portion 224 and the second portion 226. However, it is to be understood that the first 224 and second 226 portions may be connected directly. The flat hook member 220 may be comprised as the same material as the second tube sub-member 250, and in examples may be integrally formed with the second tube sub-member 250. In other examples, the flat hook member 220 may be brazed, glued, welded, adhered, or otherwise affixed to the second tube sub-member 250. In examples, a support may extend from first portion 224 into the lumen 258 of the second tube sub-member 250 in a proximal direction, and may be brazed, glued, welded, adhered, or otherwise affixed in the lumen 258. The flat hook member 220 may be sufficiently flexible to be inserted in a body cavity and to navigate a tortious path in a body to a target tissue. In examples, the flat hook member 220 is affixed to the second tube sub-member 250 in a manner to allow fluid communication between the distal opening 252 and the lumen 258. In examples, body tissue debris may be aspirated or irrigated by a fluid flow during the applications of ultrasonic vibrations through the tube sub-members 250. However, it is to be understood that the lumen 258 of the second tube sub-member 250 may be configured to allow passage of an optical device, such as a lens in operable communication with a camera or fiber-optic cable, along the lumen 258 to a targeted body tissue from an aperture in the fitting 260 or the transducer housing 1150, as in FIG. 2.

Further referencing FIGS. 5 and 6, examples of the flat hook member 220 may have a flat cross-section (e.g., a cross section that does not include a lumen). Flat hook member 220 may include one or more sharpened edges 222. Sharpened edges 222 may aid the flat hook member 220 to ablate a targeted body tissue. In examples, the flat cross section of flat hook member 220 may allow an efficient or focused application of ultrasonic energy to a target tissue, in examples wherein ultrasonic energy is conducted along the second tube sub-member 250.

Examples of first tube sub-member 270 may be brazed, glued, welded, adhered, or otherwise fixedly attached to fitting 260. As with the examples of tube sub-members 250 in FIGS. 3 and 4, examples of first tube sub-member 270 may be configured to transmit ultrasonic energy from a transducer assembly 1150, along the length of the first tube sub-member 270, and to aspirate body tissue debris and/or provide fluid irrigation. In other examples, first tube sub-member 270 may be comprised of a material, such as plastic, that is not configured to transmit sufficient ultrasonic energy to ablate a target body tissue. In such examples, the lumen 278 of first tube sub-member 270 may comprise an elongated device passage between the distal opening 276 in the first, distal end 220, and an opening in the second, proximal opening 274, configured to allow an optical device to pass from the proximal end 274 to the distal end 272 and to be positioned in or through the distal opening 256 to provide visual data on the body cavity and/or target tissue to a user.

With continued reference to FIGS. 5 and 6, fitting 260 may comprise an opening and a first lumen 262 in fluid communication with the opening in the proximal end 274 of the first tube sub-member 270, wherein the opening and the first lumen 262 are configured to allow a user to insert an optical device into the first tube sub-member 270, and to be used as a device passage. Examples of the opening and first lumen 262 may be in fluid communication with an aperture or port on the transducer housing 1151 of FIG. 2. In examples, a user may insert a fiber optic device from the housing 1151, through the device passage, to the distal opening, and to be positioned in or through the distal opening 276 to provide visual data on the body cavity and/or target tissue to a user.

As shown in FIG. 6, an example of fitting 260 also may comprise a second lumen 266 in fluid communication with a lumen 1166 of the transducer horn 1163 of the transducer assembly 1150 of FIG. 2. As shown in the example of FIG. 2, a suction force and/or fluid irrigation may be applied through the transducer assembly 1150 and the second lumen 266 to provide irrigation through one or more of the tube sub-members 250, 270 of the transmission member 200, and/or to remove body tissue debris aspirated through the transmission member 200.

Figure 7:
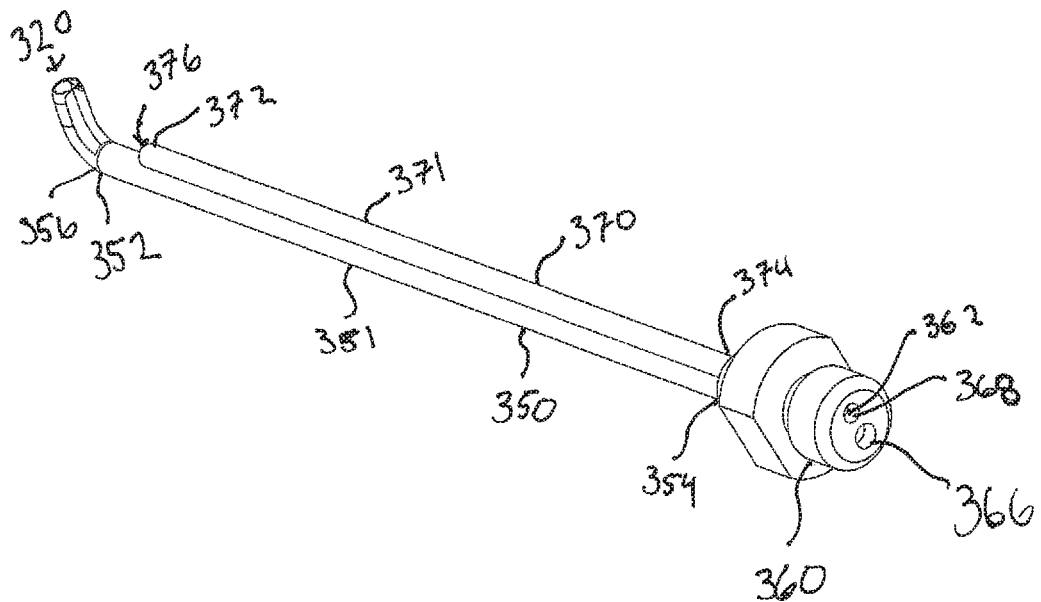
FIG. 7 is a perspective view of another example of a compound transmission member having a bent hook member consistent with the present disclosure.
Figure 8:
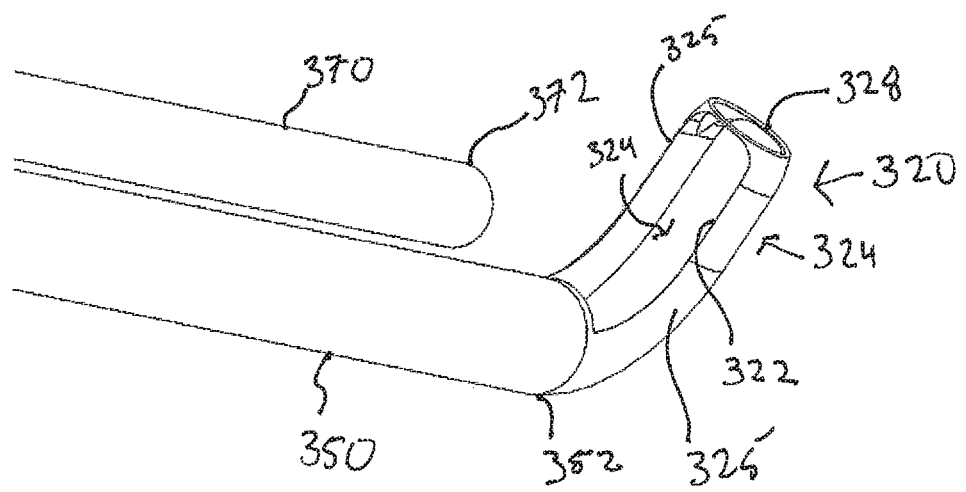
FIG. 8 is a perspective view of a distal end of the example of FIG. 7.

FIGS. 7 and 8 show an embodiment of a compound transmission member 300 having a first tube sub-member 370 and a second tube sub-member 350, affixed in a fitting 360 as in other examples herein. The first tube sub-member 370 comprises a distal end 372 and a proximal end 374. A distal opening 376 is disposed on the distal end 372 of first tube sub-member 370, and first tube sub-member 370 comprises a sidewall 371 between the distal end 372 and the proximal end 374 defining a lumen in fluid communication with the distal opening 376 and an opening at proximal end 374. Similarly, second tube sub-member 350 comprises a distal end 352 and a proximal end 354. A distal opening 356 is disposed on the distal end 352 of second tube sub-member 350, and second tube sub-member 350 comprises a sidewall 351 between the distal end 352 and the proximal end 354 defining a lumen in fluid communication with the distal opening 356 and an opening in the proximal end 354. In examples, second tube sub-member 350 may be brazed, glued, welded, adhered, or otherwise fixedly attached to fitting 360 and configured to transmit ultrasonic energy from a transducer assembly (as in 1150 in FIG. 2) along the sidewall 351, to the distal end 352 of the second tube sub-member 350. First tube sub-member 370 also may be configured to transmit and apply ultrasonic energy from a transducer assembly from a proximal end 374 to a distal end 372; however, it is to be understood that examples of one or more tube sub-members of transmission member 300 may not be configured to transmit ultrasonic energy, an example of which may be first tube sub-member 370 comprised of plastic. In examples, either or both of first 370 and second 350 tube sub-members may aspirate debris or irrigate a fluid flow during the applications of ultrasonic vibrations through the transmission member 300. The first 370 and second 350 tube sub-members are configured to be sufficiently flexible to navigate a tortious path in a body cavity to reach a target tissue.

With further reference to FIGS. 7 and 8, a cutting member comprising a bent hook member 320 may be disposed on the distal end 372 of second tube sub-member 350. An example of a bent hook member 320 may extend in a direction away from the longitudinal axis of the second tube sub-member 350. Examples of a bent hook member 320 may be comprised of the same material as the second tube sub-member 350, and in examples may be integrally formed with the second tube sub-member 350, and may be formed by removing at least one cutout portion 324 from the distal end 352 of the second tube sub-member 350 to form at least one distal sidewall 325. The at least one distal sidewall 325 preferably will be sufficiently long to be bent away from the longitudinal axis of the second tube sub-member 350 to form the bent hook member 320. In other examples, the bent hook member 320 may be a separate piece, and may be brazed, glued, welded, adhered, or otherwise fixedly attached to the second tube sub-member 350. The at least one distal sidewall 325 may include at least one sharpened edge 322 positioned to aid the bent hook member 320 to ablate a targeted body tissue. In examples, cutting edges 322 may allow an efficient or focused application of ultrasonic energy to a target tissue, in examples wherein ultrasonic energy is conducted along the second tube sub-member 350. The bent hook member 320 further may comprise a support 328 spanning a portion of the at least one cutout portion 324. In examples, the support 328 may comprise an annular shape, and may be integrally formed with the second tube sub-member 350. In other embodiments, the support 328 may be brazed, glued, welded, adhered, or otherwise fixedly attached to the at least one distal sidewall 325.

An example of bent hook member 320 may include two opposing cutout portions 324 forming two opposing distal sidewalls 325, each of which comprise a cutting edge 322. The opposing distal sidewalls 325 are bent away from the longitudinal axis of the second tube sub-member 350 to position one of the opposing cutout portions 324 to expose distal opening 356 of second tube sub-member 350 to allow maximum fluid flux into or from the lumen of second tube sub-member 350.

The bent hook member 320 may be sufficiently flexible to be inserted in a body cavity and to navigate a tortious path in a body. In examples, the bent hook member 320 is affixed to the second tube sub-member 350 in a manner to allow fluid communication between the distal opening 356 and the lumen. In examples, body tissue debris may be aspirated or irrigated by a fluid flow during the applications of ultrasonic vibrations through the tube sub-members 350, 370. However, it is to be understood that the lumen of the second tube sub-member 350 may be configured to allow passage of an optical device, such as a lens in operable communication with a camera or fiber-optic cable, along the lumen 358 to a targeted body tissue from an aperture in the fitting 360 or the transducer housing 1150, as in FIG. 2.

With reference to FIG. 7, fitting 360 may include outer threads (not shown) and may be threadably connectable to corresponding internal threads of a distal end portion of a transducer horn, as in FIG. 2. Examples of fitting 360 may comprise an opening and a first lumen 362 in fluid communication with the opening in the proximal end 374 of the first tube sub-member 370, wherein the opening and the first lumen 362 are configured to allow a user to insert an optical device into the first tube sub-member 370, and to be used as a device passage in examples where first tube sub-member 370 is comprised of a material, such as plastic, that is not configured to transmit sufficient ultrasonic energy to ablate a target body tissue. Examples of the opening and first lumen 362 may be in fluid communication with an aperture or port on the transducer housing 1151 of FIG. 2. In examples, a user may insert a fiber optic device from the housing, through the device passage to the distal opening, and to be positioned in or through the distal opening 376 to provide visual data on the body cavity and/or target tissue to a user.

With further reference to FIG. 7, an example of fitting 360 also may comprise a second lumen 366 in fluid communication with a lumen 1166 of the transducer horn 1163 of the transducer assembly 1150 of FIG. 2. As shown in the example of FIG. 2, a suction force and/or fluid irrigation may be applied through the transducer assembly 1150 and the second lumen 366 to provide irrigation through one or more of the tube sub-members 350, 370 of the transmission member 300, and/or to remove body tissue debris aspirated through the transmission member 300.

Figure 9:
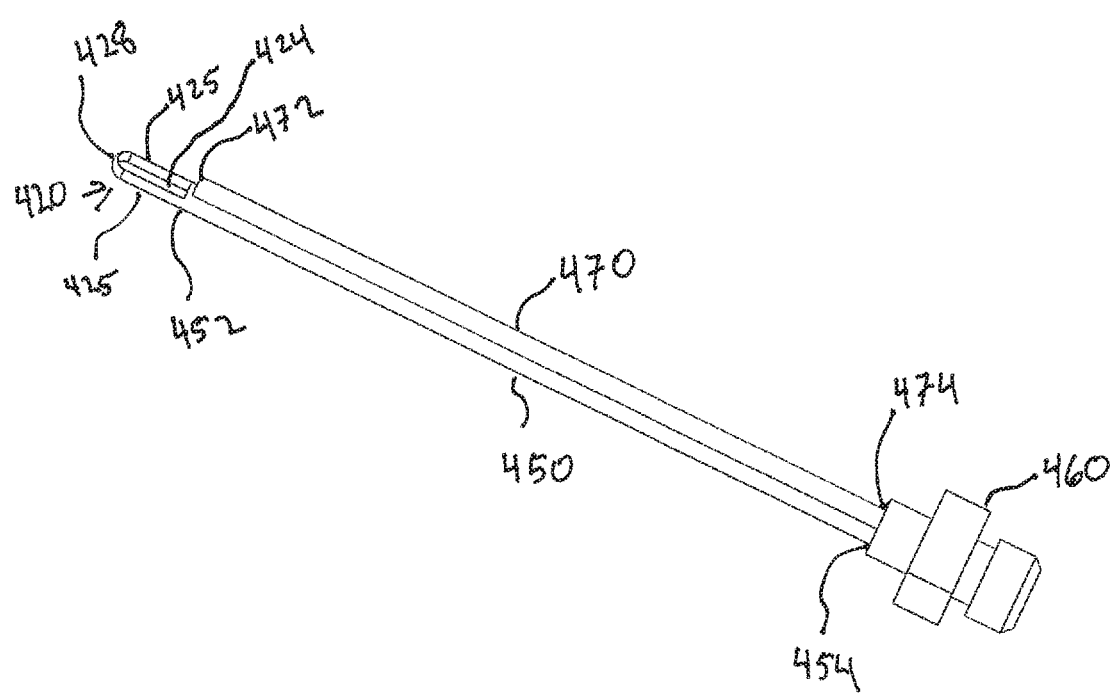
FIG. 9 is a perspective view of an example of a compound transmission member having a straight hook member consistent with the present disclosure.

FIG. 9 shows an example of a transmission member 400 similar to the exemplary transmission member 300 depicted in FIGS. 7 and 8. As shown in FIG. 9, a straight hook member 420 is disposed on the distal end 452 of the second transmission sub-member 450. As with the bent hook member 320 depicted in FIGS. 7 and 8, examples of straight hook member 420 may be comprised as the same material as the second transmission sub-member 450, and may be integrally formed with the second transmission sub-member 450, and may be formed by removing at least one cutout portion 424 from the distal end 452 of the second transmission sub-member 450 to form at least one distal sidewall 425. In other examples, the straight hook member 420 may be welded, brazed, affixed, glued, adhered, or otherwise attached to the second tube sub-member 450. The at least one distal sidewall 425 may include at least one sharpened edge positioned to aid the straight hook member 420 to ablate a targeted body tissue. The straight hook member 420 further may comprise a support 428 spanning a portion of the at least one cutout portion 424. The support 428 may be brazed, glued, welded, adhered, or otherwise fixedly attached to the at least one distal sidewall 425. In other examples, the support 428 may comprise a direct connection between two opposing distal sidewalls 425.

An example of straight hook member 420 may include two opposing cutout portions 424 forming two opposing distal sidewalls 425, each of which comprise a cutting edge.

The opposing distal sidewalls 425 extend in a direction substantially along the longitudinal axis of the second transmission sub-member 450. A support 428 connects the two opposing distal sidewalls 425. Ultrasonic energy may be transmitted from a transducer, along transmission member 400, and be applied to a target tissue by the straight hook member 420. In examples, straight hook member 420 may allow an efficient or focused application of ultrasonic energy to a target tissue. The straight hook member 420 may be sufficiently flexible to be inserted in a body cavity and to navigate a tortious path in a body.

With continued reference to FIG. 9, first transmission sub-member 470 and second transmission sub-member 450 both may brazed, welded, affixed, or otherwise attached to fitting 460, and comprised of a material configured to transmit ultrasonic energy. In this example, both first 470 and second 450 transmission sub-members may apply suction force to aspirate tissue debris. In another example, first transmission sub-member 470 may be comprised of a material, such as plastic, that is not configured to transmit sufficient ultrasonic energy to ablate a target body tissue. In this example, the lumen of second transmission sub-member 470 may comprise a device passage, like the device passage of the first sub-member 370 of the example of a transmission member 300 shown in FIGS. 7 and 8.

Figure 10:
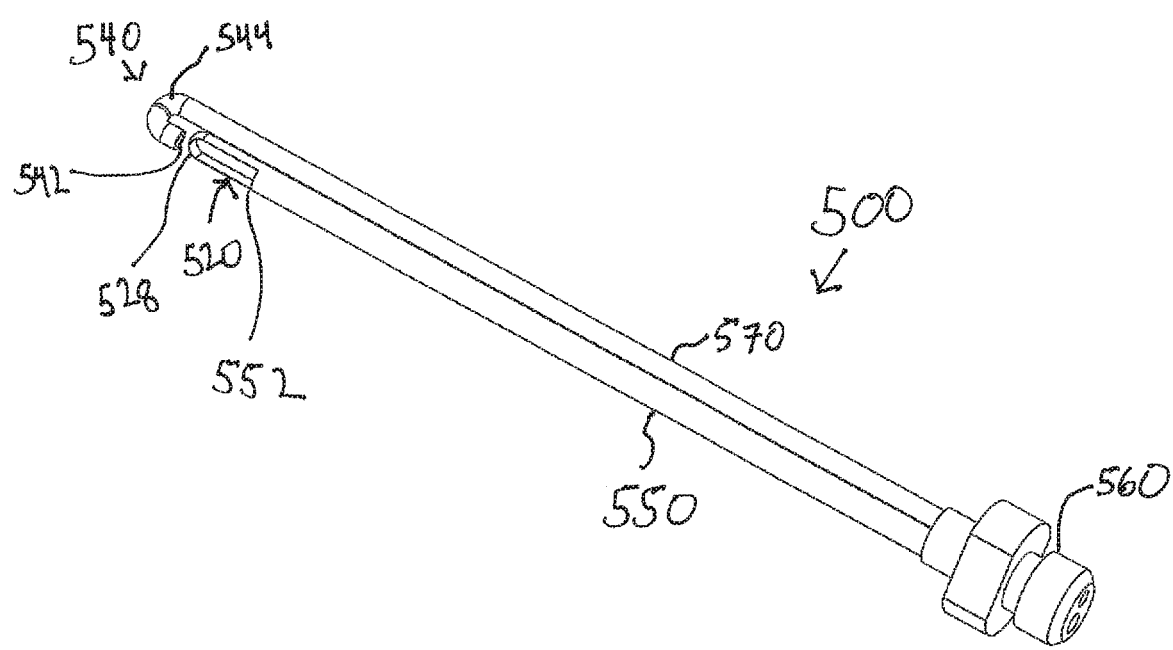
FIG. 10 is a perspective view of another example of a compound transmission member having a straight hook member according to the present disclosure.

FIG. 10 depicts another example of a transmission member 500 comprising a first tube sub-member 570 and a second tube sub-member 550. As with the exemplary transmission member 400 shown in FIG. 9, a straight hook member 520 is disposed on the distal end 542 of second tube sub-member 550. A bent configuration 540 is disposed on the distal end 542 of first tube sub-member 570. Bent configuration 540 extends distally past the support 528 of the straight hook member 520, and comprises a curved portion 544 and an aperture 542. The curved portion 544 positions the aperture 542 along the longitudinal axis of the second tube sub-member 550 and straight hook member 520. The bent configuration 540 includes a lumen in fluid communication with the aperture 542 and the lumen of first tube sub-member 570.

Bent configuration 540 may be integrally formed and of the same material as the first tube sub-member 570. Another example of bent configuration 540 may be brazed, glued, welded, adhered, or otherwise fixedly attached to the distal end 542 of the first tube sub-member. Examples of bent configuration 540 and first tube sub-member 570 may be configured to transmit ultrasonic energy from a transducer, and may provide a suction force to aspirate tissue debris ablated by straight hook member 520. In examples, second tube sub-member 550 and straight hook member 520 also may be configured to transmit and apply ultrasonic energy from the transducer, and second tube sub-member 550 may also provide a suction force to aspirate tissue debris.

With further reference to FIG. 10, another example of transmission sub-member 500, second tube sub-member 570 and bent configuration 540 may comprise a material, such as plastic, that is not configured to transmit sufficient ultrasonic energy to ablate tissue. In this example, the lumen of second tube sub-member 570 and bent configuration 540 may comprise a device passage, like the device passage of the first tube sub-member 370 of the example of a transmission member 300 shown in FIGS. 7 and 8.

Figure 11:
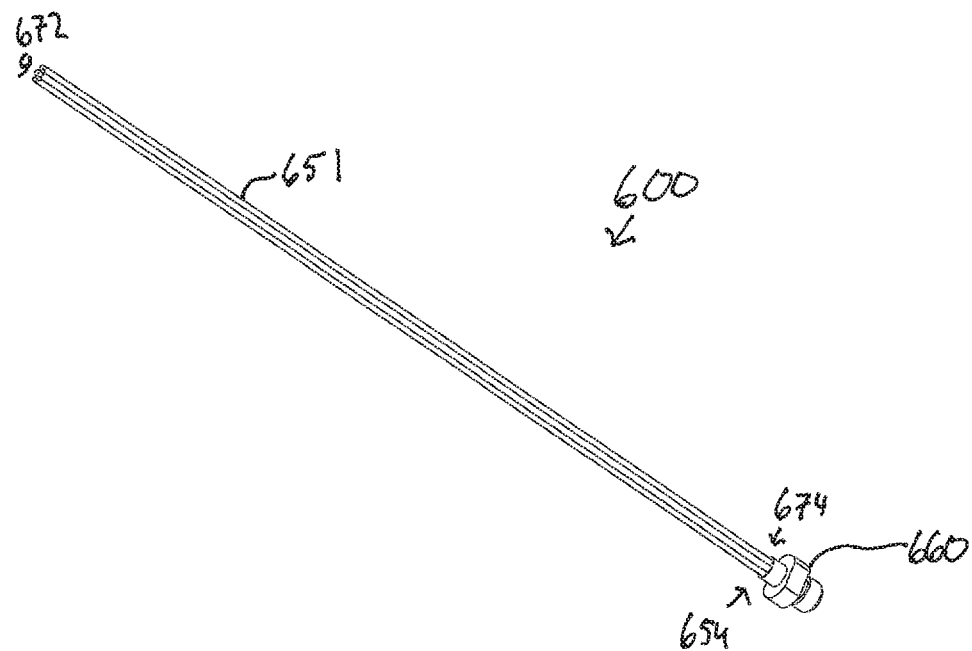
FIG. 11 is a perspective view of another example of a compound transmission member consistent with the present disclosure.
Figure 12:
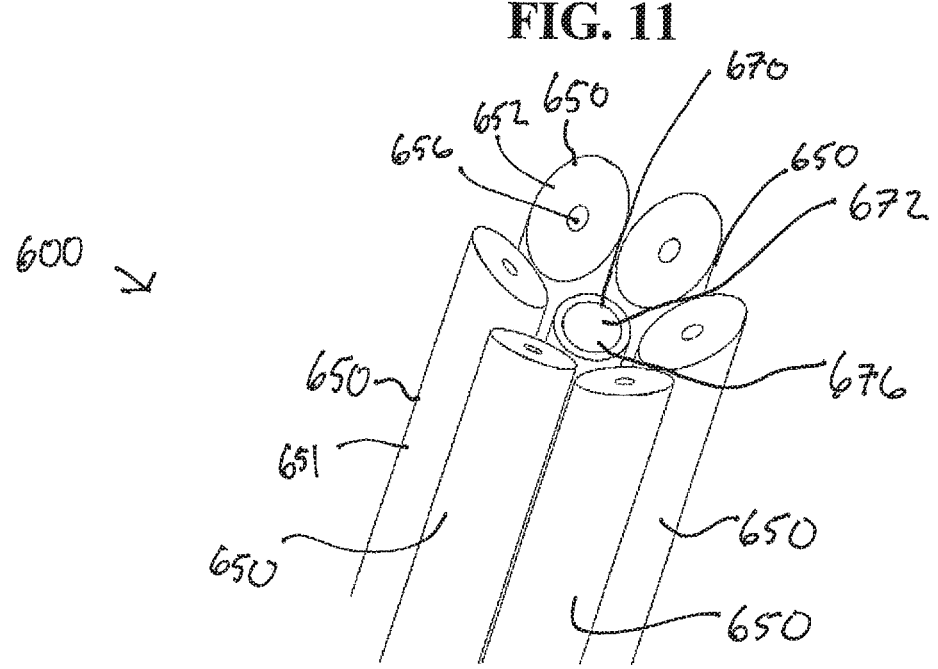
FIG. 12 is a perspective view of a distal end of the example of FIG. 11.

FIGS. 11 and 12 show an example of a transmission member 600 comprising six transmission tube sub-members 650, each of which comprise an elongate tube having a sidewall 651, a proximal end 654, and a distal end 652 which is configured to be inserted into a body cavity. A lumen is defined by the each elongate tube, and establishes fluid communication between an opening in the proximal end 654 and a distal opening 656 disposed in the distal end 652 of each transmission tube sub-member 650. Each transmission tube sub-member is comprised of a material, such as metal, that transmits ultrasonic energy, and is configured to transmit sufficient ultrasonic energy from a transducer to distal ends 652 of the transmission tube sub-members 650 to ablate a target tissue. The proximal ends 654 of the transmission tube sub-members 650 may be brazed, glued, welded, adhered, or otherwise fixedly attached to a fitting 660. The fitting 660 may include external threading, not shown, configured to co-act with internal threading, not shown, on a distal end portion 1165 of a transducer horn 1163, as in FIG. 2. The transmission tube sub-members 650 further have sufficient flexibility to facilitate the passage of the transmission member through a tortuous lumen or path within a patient. For example, in some examples, a compound transmission member 600 can have a suitable flexibility such that at least a portion of the transmission member can elastically (e.g., not permanently) deform within the tortuous anatomical structure.

With continued reference to FIGS. 11 and 12, the distal ends 652 of the transmission tube sub-members 650 may be angled with respect to a cross-section perpendicular to the longitudinal axis of the transmission member 600. The angle of the distal ends 652, and arrangement of the transmission tube sub-members 650 may be configured to focus ultrasonic energy at a point that is distal from the distal ends 652 of the transmission tube sub-members 650, and may create a shockwave of ultrasonic energy at that point. Focusing ultrasonic energy at a point that is distal from the distal ends 652 may aid in efficiently applying ultrasonic energy to a target body tissue. As in other examples, the lumens of transmission tube sub-members 650 may aspirate body tissue debris, and provide irrigation.

With further reference to FIGS. 11 and 12, the transmission sub-members 650 may be radially disposed around a second tube sub-member 670. The second tube sub-member 670 comprises an elongate tube having a sidewall, a proximal end 674, and a distal end 672 which is configured to be inserted into a body cavity. A lumen is defined by the elongate tube, and establishes fluid communication between an opening in the proximal end 674 and a distal opening disposed in the distal end 672 of the second tube sub-member 670. The proximal end 674 of the second tube sub-member 670 may be brazed, glued, welded, adhered, or otherwise fixedly attached to a fitting 660.

With continued reference to FIGS. 11 and 12, examples of second tube sub-member 670 may be comprised of a material, such as metal, that transmits ultrasonic energy, and is configured to transmit sufficient ultrasonic energy from a transducer to distal end 672 of the second tube sub-member 670. In such examples, second tube sub-member 670 may aspirate body tissue debris, and provide irrigation to the target tissue.

With continued reference to FIGS. 11 and 12, in other examples, second tube sub-member 670 may be comprised of a material, such as plastic, that is not configured to transmit sufficient ultrasonic energy to ablate a target tissue. In such examples, the second tube sub-member 670 may comprise a device passage configured to allow an optical device to pass from the proximal end 674 to the distal end 672 and to be positioned in or through the distal opening 656 to provide visual data on the body cavity and/or target tissue to a user.

With further reference to FIGS. 11 and 12, transmission member 600 may be heated by ultrasonic energy. Fluid passing through the lumens of transmission tube sub-members 650 and/or second sub-member 670 may provide cooling to the transmission member 600. However, it is to be understood that examples, exist wherein one or more sub-members of a transmission member may be thin wire sub-members, which are configured to transmit ultrasonic energy, but have no lumens. In such examples the distal ends of the wire sub-members may transmit ultrasonic energy to a target tissue. Wire sub-members may be included in embodiments of transmission members having one or more tube sub-members as well.

Various examples of transmission members may comprise an outer sheath that encircles at least a portion of the transmission member. Other examples may not comprise an outer sheath.

Various examples of transmission members may comprise one or more sub-members having sufficient flexibility to navigate a tortious path through a body cavity to reach a target body tissue to be ablated. As shown in FIG. 1, examples of transmission members may have a preferable total outside diameter D1 in a cross-section perpendicular to the longitudinal axis of the transmission member. Each tube sub-member may have a preferable inner diameter D2 of the lumens therein in a cross-section perpendicular to the longitudinal axis. TABLE 1, below, shows various preferable total outside diameters and inner diameters for transmission members having various numbers of tube sub-members.

cavity and/or target tissue to a user. Preferably, examples of tube sub-member 820 comprising a device passage 850 are comprised of a material, such as plastic, that is not configured to transmit ultrasonic energy from the transducer horn to the distal end of the tube sub-member 820, but is sufficiently flexible to navigate a tortious body passage. The tube sub-member 820 comprises a device passage 850 and is fluidly connected to a port 852. The port 852 may be disposed on the fitting 830, or on the housing of the transducer assembly, not shown.

Figure 13:
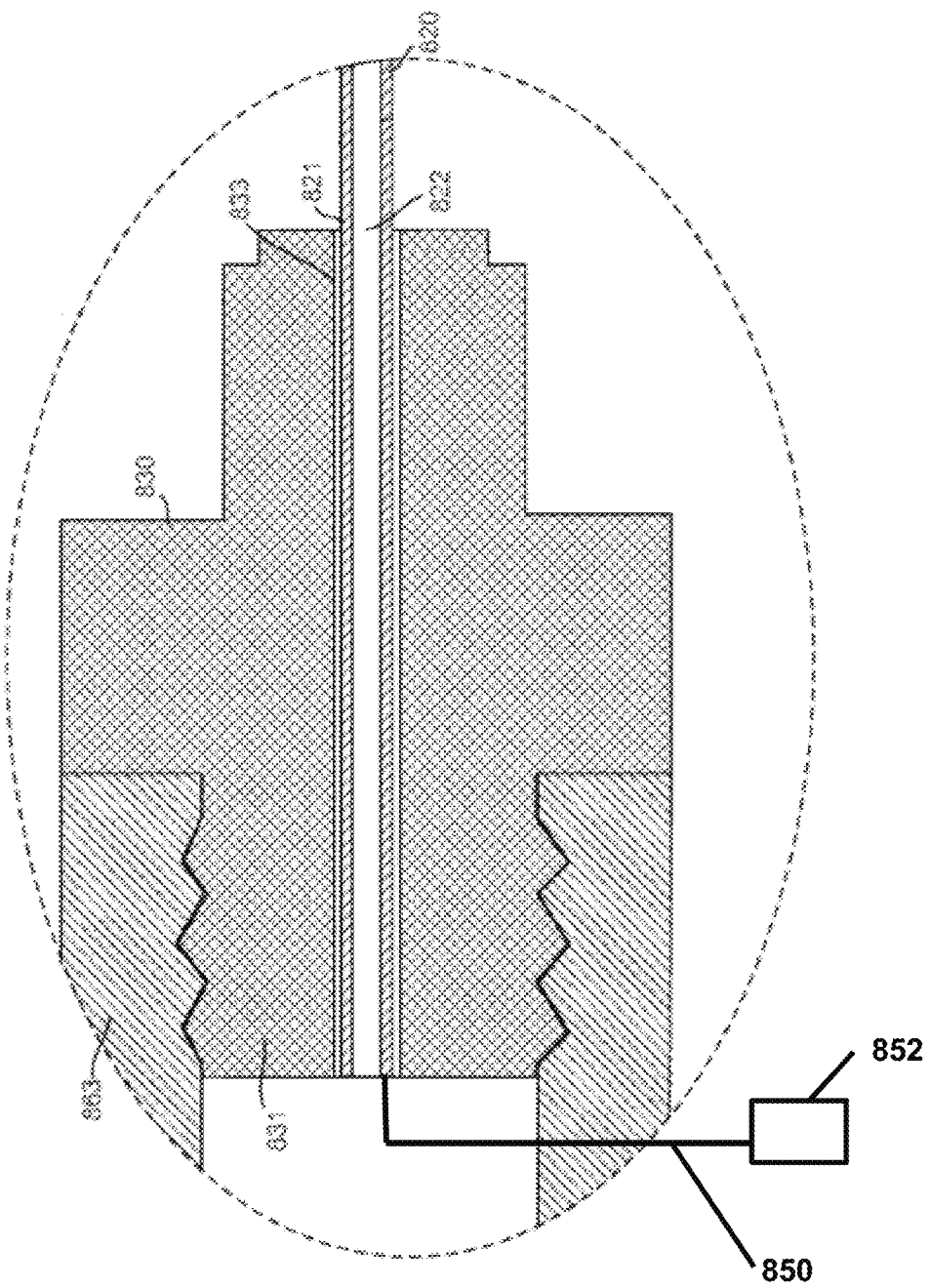
FIG. 13 is a schematic representation of a fitting consistent with the present disclosure.
Figure 14:
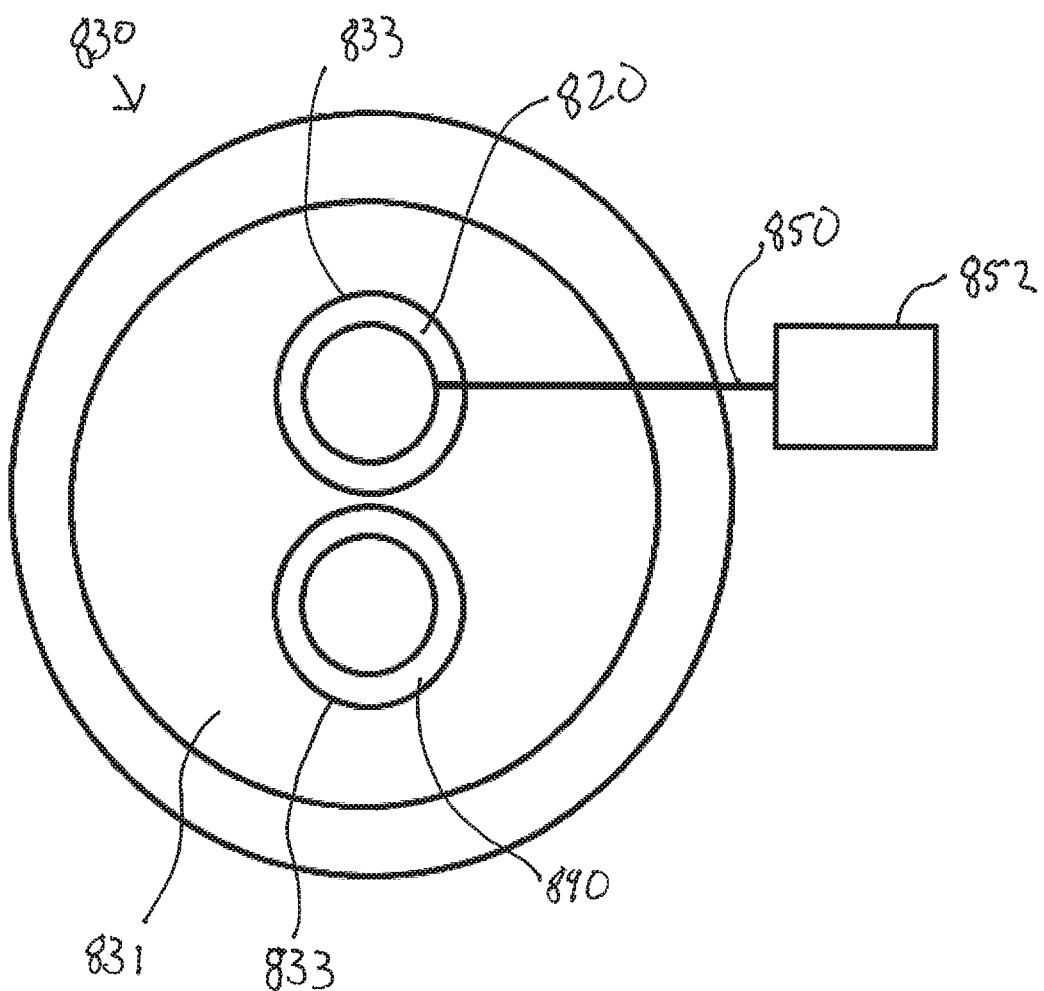
FIG. 14 is schematic representation of a fitting according to FIG. 13.

FIG. 14 show a schematic representation consistent with the fitting 830 of FIG. 13, viewed from the proximal end 831. Fitting 830 comprises two lumens 833 configured to fixedly attach to a first tube sub-member 820, and a second tube sub-member 890. The first tube sub-member 820 comprises a device passage 850 and is fluidly connected to a port 852. The port 852 may be disposed on the fitting 830, or on the housing of the transducer assembly, not shown. The second tube sub-member 890 may be configured to transmit ultrasonic energy, as described above.

Figure 15:
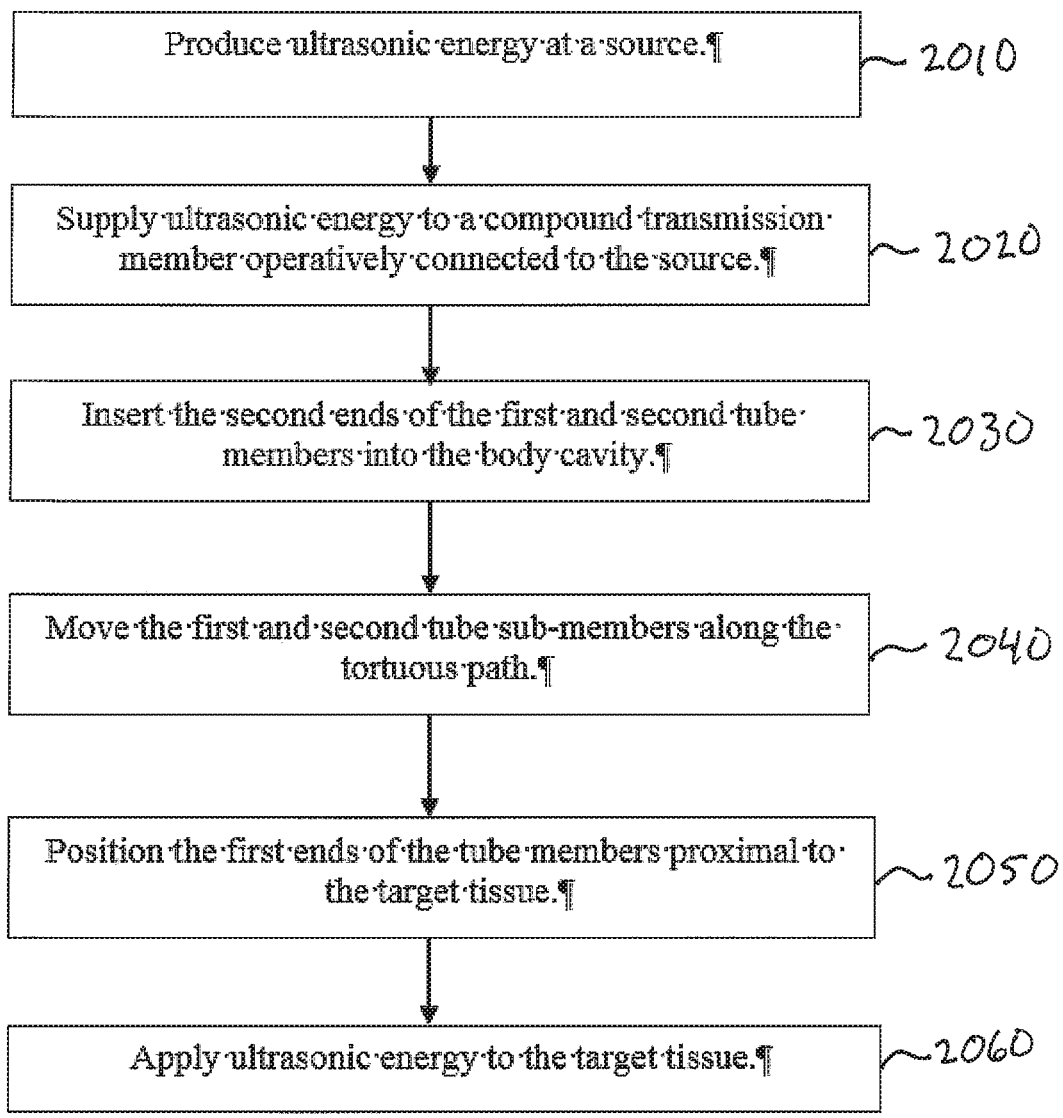
FIG. 15 is a flow chart of an exemplary method for ablating a target tissue consistent with the present disclosure.

FIG. 15 is a flow chart of an exemplary method for ablating a target tissue consistent with the present disclosure. Step 2010 comprises producing ultrasonic energy at a source. Step 2020 comprises supplying ultrasonic energy to a compound transmission member operatively connected to the source. The compound transmission member may comprise a first tube sub-member and a second tube sub-member, each comprising a first end having a first opening and a second end having a second opening, wherein the first

TABLE 1

| Total outside diameter of transmission member | Inner diameter of example with two tube sub-members | Inner diameter of example with three tube sub-members | Inner diameter of example with four tube sub-members | Inner diameter of example with five tube sub-members | Inner diameter of example with six tube sub-members | Inner diameter of example with seven tube sub-members |
|---|---|---|---|---|---|---|
| 4 mm | 2 mm | 1.8 mm | 1.6 mm | 1.4 mm | 1.3 mm | 1.2 mm |
| 3 mm | 1.5 mm | 1.3 mm | 1.2 mm | 1.1 mm | 0.9 mm | 0.8 mm |
| 2 mm | 1 mm | 0.9 mm | 0.8 mm | N/A | N/A | N/A |

FIG. 13 is a cross-sectional schematic representation of an exemplary fitting 830 consistent with the present disclosure. Proximal portion 831 of fitting 830 is threadably coupled to a transducer horn 863 via corresponding external threads on the proximal portion 831 of the fitting 830 and internal threads in the transducer horn 863. The cross-sectional representation shows a single tube sub-member 820 passing through a lumen 833 in the fitting 830, but it should be understood that multiple sub-members may pass through lumens in the fitting. In examples, the fitting may comprise a lumen corresponding to each sub-member of the transmission member, so that only one sub-member passes through a lumen. In other examples, the more than one tube sub-member may pass through a single lumen in the fitting 830.

With continued reference to FIG. 13, the lumen 833 passes through the fitting, and allows the lumen of the tube sub-member to be in fluid communication with the transducer assembly.

As shown in FIG. 13, tube sub-member 820 comprises a device passage 850. As schematically shown, an aperture or port 852 in the fitting 830 or on the transducer housing (not shown) may allow a user to insert a fiber optic device, or other optical device, through the device passage 850 and lumen 822 of the tube sub-member 820, to the distal opening of the sub-member 820, to provide visual data on the body opening is in fluid communication with the second opening, and wherein at least the first tube sub-member is configured to transmit ultrasonic energy. The compound transmission member also may comprise a fitting configured to receive the first ends of the tube sub-members. The first and second tube sub-members are sufficiently flexible to move along a tortuous path in a body cavity. Step 2030 comprises inserting the second ends of the first and second tube members into the body cavity. Step 2040 comprises moving the first and second tube sub-members along the tortuous path. Step 2050 comprises positioning the first ends of the tube members proximal to the target tissue. Step 2060 comprises applying ultrasonic energy to the target tissue.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

The invention claimed is:

1. A compound transmission member comprising:
    a first tube sub-member and a second tube sub-member, each comprising:
    a first end having a first opening and a second end having a second opening, wherein the first opening is in fluid communication with the second opening, and
    wherein at least the first tube sub-member is configured to transmit ultrasonic energy;
    a fitting configured to receive the first ends of the tube sub-members; and
    a third through seventh tube sub-member configured to transmit ultrasonic energy, each comprising a first end having a first opening and a second end having a second opening, wherein the first opening is in fluid communication with the second opening;
    wherein the second tube sub-member defines an elongated device passage between the first opening and the second opening configured to allow an optical device to pass from the first end to the second end;
    wherein the second ends of the first and third-through seventh tube sub-members are configured to focus ultrasonic energy at a point that is distal from the second ends of the first-through seventh tube sub-member;
    wherein the fitting is configured to receive the first ends of the tube sub-members and comprises an opening and a first lumen in fluid communication with the opening and the elongated device passage; and
    wherein the opening and the first lumen are configured to allow a user to insert an optical device into the device passage.

2. The compound transmission member according to claim 1, wherein the first tube sub-member and the second tube sub-member are attached to the fitting.

3. The compound transmission member according to claim 1, further comprising an outer sheathing enclosing at least a portion of the compound transmission member.

4. The compound transmission member according to claim 1, further comprising a cutting tool extending from the second end portion of the first tube sub-member and configured to ablate a target tissue.

5. The compound transmission member according to claim 4, wherein the cutting tool is welded, brazed, or glued to the first tube sub-member.

6. The compound transmission member according to claim 4, wherein the cutting tool comprises a flat hook member.

7. The compound transmission member according to claim 4, wherein the cutting tool comprises a bent tube hook member, the bent tube hook member comprising:
    an extension portion extending from the second end portion of the first tube sub-member in a direction away from a longitudinal axis of the first tube sub-member; and
    a first cutout portion in the extension portion defining a cutting edge.

8. The compound transmission member according to claim 4, wherein the cutting tool comprises a straight tube hook member, the straight tube hook member comprising:
    an extension portion extending from the second end portion of the first tube sub-member in a direction along a longitudinal axis of the first tube sub-member; and
    a first cutout portion in the extension portion defining a cutting edge.

9. The compound transmission member according to claim 8, wherein the second tube sub-member comprises a bent configuration extending from the second end of the second sub-member,
    wherein the bent configuration defines a lumen in fluid communication with the first opening in the first end of the second tube sub-member; and
    an end opening in fluid communication with the lumen of the bent configuration, wherein the end opening is oriented along the longitudinal axis of the first tube sub-member.

10. The compound transmission member according to claim 1, wherein the first and second tube sub-members define an outer diameter of at least 1 millimeters, and no more than 2 millimeters.

11. The compound transmission member according to claim 1, wherein each tube sub-member defines an outer diameter of at least 0.9 millimeters and no more than 1.8 millimeters.

12. The compound transmission member according to claim 1, wherein each tube sub-member defines an outer diameter of at least 0.8 millimeters and no more than 1.6 millimeters.

13. The compound transmission member according to claim 1, wherein each tube sub-member defines an outer diameter of at least 1.1 millimeters and no more than 1.4 millimeters.

14. The compound transmission member according to claim 1, wherein each tube sub-member defines an outer diameter of at least 0.9 millimeters and no more than 1.3 millimeters.

15. The compound transmission member according to claim 1, wherein each tube sub-member defines an outer diameter of at least 0.8 millimeters and no more than 1.2 millimeters.

16. The compound transmission member according to claim 1, further comprising at least one additional tube sub-member, wherein each tube sub-member is a wire sub-member defining an outer diameter of at least 0.1 millimeters and no more than 1.0 millimeters.

17. The compound transmission member according to claim 1, wherein the fitting comprises a first end and a second end,
    wherein the first end of the fitting is configured to receive the first ends of the tube sub-members; and
    wherein the second end is configured to operatively engage a transducer horn.

18. The compound transmission member according to claim 1, wherein at least the first tube sub-member is configured to apply a suction force during ablation of a target tissue.

19. The compound transmission member according to claim 1, wherein the tube sub-members are arranged in a bundle.

20. A compound transmission member comprising:
    a first tube sub-member and a second tube sub-member, each comprising:
    a first end having a first opening and a second end having a second opening, wherein the first opening is in fluid communication with the second opening, and
    wherein at least the first tube sub-member is configured to transmit ultrasonic energy;
    a fitting configured to receive the first ends of the tube sub-members; and
    a cutting tool extending from the second end of the first tube sub-member and configured to ablate a target tissue, the cutting tool comprising a straight tube hook member, the straight tube hook member comprising:
an extension portion extending from the second end of the first tube sub-member in a direction along a longitudinal axis of the first tube sub-member; and
a first cutout portion in the extension portion defining a cutting edge, wherein the second tube sub-member comprises:
a bent configuration extending from the second end of the second tube sub-member, the bent configuration defining a lumen in fluid communication with the first opening in the first end of the second tube sub-member; and
an end opening in fluid communication with the lumen of the bent configuration, wherein the end opening is oriented along the longitudinal axis of the first tube sub-member.

* * * * *